United States Patent
MacAllister

(10) Patent No.: US 10,946,011 B2
(45) Date of Patent: Mar. 16, 2021

(54) STABLE ORAL LIQUID FORMULATION OF TRIMETAZIDINE

(71) Applicant: Martin Pharmaceuticals Inc., New York, NY (US)

(72) Inventor: Thomas MacAllister, Arlington, VA (US)

(73) Assignee: Martin Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/277,986

(22) Filed: Feb. 15, 2019

(65) Prior Publication Data

US 2019/0255039 A1  Aug. 22, 2019

Related U.S. Application Data

(60) Provisional application No. 62/788,881, filed on Jan. 6, 2019, provisional application No. 62/685,384, filed on Jun. 15, 2018, provisional application No. 62/632,389, filed on Feb. 19, 2018.

(51) Int. Cl.

| | |
|---|---|
| *A61K 31/495* | (2006.01) |
| *A61K 47/14* | (2017.01) |
| *A61K 47/24* | (2006.01) |
| *A61K 9/08* | (2006.01) |
| *A61K 47/36* | (2006.01) |
| *A61K 9/00* | (2006.01) |
| *A61K 47/02* | (2006.01) |
| *A61K 47/26* | (2006.01) |
| *A61K 47/12* | (2006.01) |

(52) U.S. Cl.
CPC .......... *A61K 31/495* (2013.01); *A61K 9/0095* (2013.01); *A61K 9/08* (2013.01); *A61K 47/02* (2013.01); *A61K 47/12* (2013.01); *A61K 47/14* (2013.01); *A61K 47/24* (2013.01); *A61K 47/26* (2013.01); *A61K 47/36* (2013.01)

(58) Field of Classification Search
CPC .................................................... A61K 31/495
USPC ..................................................... 514/252.12
See application file for complete search history.

(56) References Cited

U.S. PATENT DOCUMENTS

2010/0022551 A1*  1/2010  Rahman ............... A61K 31/495
                                                      514/252.12

OTHER PUBLICATIONS

Cutaia, Kara; Chablani, Lipika; and Zhao, Fang (2018). "Basics of Compounding: Vehicles for Compounded Oral Liquid Medications: A Review." International Journal of Pharmaceutical Compounding 22.6, 480-489.

* cited by examiner

*Primary Examiner* — Raymond J Henley, III
(74) *Attorney, Agent, or Firm* — Thomas W. MacAllister

(57) ABSTRACT

Disclosed is a stable oral liquid pharmaceutical composition of trimetazidine having a pH of about pH 4 to about pH 8, comprising a therapeutically effective amount of trimetazidine or a pharmaceutically acceptable salt thereof, one or more orally acceptable buffers, and one or more orally acceptable preservatives that is effective in said pH range. Also disclosed are methods of treating patients with stable oral liquid pharmaceutical composition. The pharmaceutical composition is particularly suitable for treating a patient having a condition treatable by trimetazidine, such as cirrhosis and renal deficiency, and who has a decreased tolerance for acidic or highly basic oral solutions.

17 Claims, No Drawings

STABLE ORAL LIQUID FORMULATION OF TRIMETAZIDINE

CROSS-REFERENCE TO RELATED APPLICATIONS

The present application is a non-provisional of and claims the benefit of U.S. Provisional Application No. 62/788,881, filed Jan. 6, 2019, U.S. Provisional Application No. 62/685,384, filed Jun. 15, 2018, and U.S. Provisional Application No. 62/632,389, filed Feb. 19, 2018. Each of the above-referenced applications is incorporated herein by reference in its entirety.

BACKGROUND OF THE INVENTION

The invention relates to a stable oral liquid formulation of the pharmaceutical agent trimetazidine. Trimetazidine (1-(2, 3,4-trimethoxybenzyl)piperazine) ("TMZ") was first approved for use (as its hydrochloride salt) in Europe in 1978 under the tradename Vastarel® and is currently marketed in a number of countries, including Bulgaria, Cyprus, the Czech Republic, Denmark, Estonia, France, Germany, Greece, Hungary, Ireland, Italy, Latvia, Lithuania, Luxembourg, Malta, Poland, Portugal, Romania, Slovakia, Slovenia, and Spain. An anti-ischemic compound, TMZ is principally used in the treatment of angina pectoris. The drug has never been approved by the U.S. Food and Drug Administration.

TMZ exerts its positive effects on cardiac ischemia through preventing the ATP level in cells from decreasing by maintaining proper energy metabolism of cells in a hypoxic or ischemic state, thereby guaranteeing normal functioning of the ion pump and normal operation of the transmembrane sodium-potassium flow and maintaining a stable internal environment of cells. The potential mechanisms of action for TMZ in myocardial ischemia are as follows (DiNapoli 2008):

Metabolic efficiency: shifting of ATP production to glucose oxidation, a more energetically efficient pathway;
Protection of endothelial function (increase in endothelial nitric synthase activity and nitric oxide availability; reduction in endothelin-1);
Modulation of the myocardial inflammatory reaction (reduction of neutrophil infiltration and activation);
Limitation of accumulation of $Na^+$ and $Ca^{2+}$ and intracellular acidosis;
Reduction in necrotic and apoptotic cell death;
Preservation of mitochondrial functions (reduction in mitochondrial permeabilization); and/or
Protection against toxicity induced by oxygen free radicals.

Various formulations of TMZ are known in the art. Currently available formulations are 20 mg immediate release tablet and 35 mg modified release tablets. Typical dosing regiments are 20 mg three times per day or 35 mg twice per day. In addition, an oral solution of TMZ was available (marketed under the Vastarel brand) that contained 20 mg/mL (2%) trimetazidine dichlorohydrate in methyl parahydroxybenzoate, propyl parahydroxybenzoate, propylene glycol and purified water purified water. That composition was neither buffered nor pH-adjusted and so would had a pH of approximately 3.

There is also in the patent literature a published Chinese patent application that relates to oral trimetazidine formulations that have been pH adjusted to a pH of about 6.5 to 8. In the absence of buffer, those formulations rely on the buffering capacity of the active ingredient, which has an acidic pKa at about 4.45 and a basic pKa2 at about 9.14, predicting limited buffering capacity in the selected pH range. Consistently, the Chinese application discloses very high concentrations of TMZ, generally exceeding 10% (100 mg/mL).

SUMMARY OF THE INVENTIONS

The present invention is direct to a stable oral liquid pharmaceutical composition of trimetazidine having a pH of about pH 4 to about pH 8, comprising a therapeutically effective amount of trimetazidine or a pharmaceutically acceptable salt thereof, one or more orally acceptable buffers, and one or more orally acceptable preservatives that is effective in said pH range. In certain embodiments, the oral composition has a pH range of between about 4 and about 8, but more preferably between about 5 and about 7 and most preferably between pH of about 5.5 and about 6.5.

Other embodiments of the invention are directed to methods of treating patients with stable oral liquid pharmaceutical composition. The pharmaceutical composition is particularly suitable for treating a patient having a condition treatable by trimetazidine, such as cirrhosis and renal deficiency, and who has a decreased tolerance for acidic or highly basic oral solutions.

DETAILED DESCRIPTION OF THE INVENTION

The inventive compositions are uniquely adapted to treat subjects, in particular subjects suffering from liver cirrhosis, who have a decreased tolerance for acidic or highly basic oral solutions. Such intolerance could arise, for example, from a dysfunction of the mucous membranes of the gastrointestinal tract or due to the presence of esophageal varices, which may bleed or are at risk for bleeding. In that regard, it is important that the present compositions have a pH range of between about 4 and about 8, but more preferably between about 5 and about 7 and most preferably between pH of about 5.5 and about 6.5. In preferred embodiments, the pharmaceutical composition of the invention has a pH of lower than 7 in order to avoid overly "caustic" formulations and to avoid a "slimy" characteristic that may occur at higher pH values. For most subjects, low pH products are not a problem. In fact, carbonated beverages typically have a very acidic pH of around 3. For subjects with impaired gastrointestinal tracts, this can be problematic and, thus, the inventive compositions are beneficially employed.

Patients suffering from liver cirrhosis often develop esophageal varices due to portal hypertension and are especially suitably treated with the inventive compositions. Thus, patients with decompensated cirrhosis, suffering from chronic liver failure or acute-on-chronic liver failure may also be treated with the inventive compositions. Patients with advance cirrhosis may also develop kidney dysfunction that may manifest, for example, as hepatorenal syndrome.

Trimetazidine is principally eliminated by renal excretion and so exposure to the drug is enhanced in patients with renal insufficiency. Thus, in order to maintain appropriate dosing (without over-dosing), doses of trimetazidine should be reduced in order to maintain consistent levels of exposure.

In certain embodiments, a subject to be administered and treated with a composition of the present invention has renal dysfunction or impairment or is at risk of such dysfunction or impairment due to a condition such as liver cirrhosis. The degree of renal dysfunction or impairment will typically vary from subject to subject, but in preferred embodiments, the degree of dysfunction or impairment will be moderate to severe, or the subject will be at risk of developing moderate or severe renal impairment. In certain cases, subjects will have serum creatinine levels in excess of 1.5 mg/dL, or in excess of 2 mg/dL. In particular, subjects treatable according to the invention include subjects having moderate to severe renal dysfunction. In most cases, subjects will have a creatinine clearance rate of less than 60 ml/min and in many cases less than 30 mL/min.

In general, the present invention is directed to a stable oral liquid pharmaceutical composition of trimetazidine having a pH of about pH 4 to about pH 8, comprising a therapeutically effective amount of trimetazidine or a pharmaceutically acceptable salt thereof, one or more orally acceptable buffers, and one or more orally acceptable preservatives that is effective in said pH range. The liquid formulation is generally an aqueous formulation, using sterile water for example, and or saline, but other orally acceptable liquids can be used.

While certain embodiments of the present invention may contain one or more pharmaceutically active agents in addition to trimetazidine, preferred embodiments have a therapeutically effective amount of trimetazidine or a pharmaceutically acceptable salt thereof as the only pharmaceutically active agent.

Embodiments of the compositions of the invention are also uniquely adapted for "infinite dosing." Unlike a tablet or capsule, for example, liquid formulations can be dosed up or down in very small increments. For example, a 20 mg tablet can only accurately deliver 20 mg. A 2 mg/mL solution can be used to accurately deliver drug in 0.1 to 0.5 mg increments, depending on the sophistication of the delivery system. Some metered dosing systems can accurately deliver volumes as small as 0.05 mL increments. A syringe, for example, may be used to accurately deliver volumes in 0.1 mL increments, and a graduated plastic cap may be used to deliver volumes in increments of 0.5 mL.

Embodiments of the compositions according to the invention are stable at room temperature. This stability is exhibited not only in that the ingredients of the compositions do not degrade, but also in that they do not allow any significant microbial growth, meaning that they also do not require refrigeration. Many antimicrobial agents are less effective or even ineffective at neutral pH. This is problematic in that low pH itself is also a potent antimicrobial factor. Compositions at or near neutral pH are particularly at risk of not being pharmaceutically suitable from the perspective of microbiology.

Embodiments of the present compositions advantageously contain at least one preservative that is orally acceptable. Orally acceptable preservatives are generally those listed on the Inactive Ingredient list maintained by the United States FDA (https://www.accessdata.fda.gov/scripts/cder/iig/) or by other regulatory agencies that review the marketing and approval of pharmaceutical products. In certain embodiments, an orally acceptable preservative is one that is contained in a product that has previously been approved by the FDA in an oral formulation for a pharmaceutical product. The amount of an orally acceptable preservative in a composition according to the invention typically does not exceed the maximum daily exposure provided by the already-approved formulations. This amount may be termed the maximum allowable amount. In certain embodiments, the composition of the present inventions comprises two or more orally acceptable preservatives.

The minimum amount of the one or more orally acceptable preservatives is determined by measuring effectiveness. Thus, the minimum amount may also be referred to as the minimum effective amount. The effectiveness of an orally acceptable preservative or combinations thereof can be determined using standard antimicrobial preservative effectiveness testing, such as the United States Pharmacopeia (USP) method <51> in which *Escherichia coli, Pseudomonas aeruginosa, Staphylococcus aureus, Candida albicans* and *Aspergillus brasiliensis* are inoculated into samples and monitored for growth over 28 days. The pharmaceutical formulation of the present invention fall within Category 3 products, as described below, and so they must meet the criteria for Category 3 products, enumerated below.

USP 51 Product Categories
  Category 1: Injections, other parenterals including emulsions, otic products, sterile nasal products, and ophthalmic products made with aqueous bases or vehicles.
  Category 2: Topically used products made with aqueous bases or vehicles, nonsterile nasal products, and emulsions, including those applied to mucous membranes.
  Category 3: Oral products other than antacids, made with aqueous bases or vehicles.
  Category 4: Antacids made with aqueous bases.

USP 51 Overview
  The product is separated out into 5 containers, each being challenged with one of the 5 method-specified microorganisms (*S. aureus* ATCC 6538, *E. coli* ATCC 8739, *P. aeruginosa* ATCC 9027, *C. albicans* ATCC 10231, and *A. brasiliensis* ATCC 16404) at a concentration of >1×10$^5$ CFU/ml.
  The initial concentration of each microorganism is determined by inoculating a control substance and using standard dilution and plating techniques.
  At the time of test initiation, a separate volume, typically 1 ml, of the product is diluted in a volume of chemical neutralizer broth, to be used in the neutralization and recovery validation.
  The inoculated product is held at room temperature for a period of no less than 28 days.
  The product is evaluated at specific intervals within the 28-day period. Evaluation intervals depend on the category of the product specified by the method. Click here for USP <51> product categories.
  At each contact time, the inoculated product is chemically neutralized and plated using standard dilution and plating techniques.
  After 48 hours of incubation, surviving microorganisms are counted, and the log reduction of each microorganism at each interval is reported.
  The effectiveness of the preservative system is determined based on the USP <51> passing criteria.

USP <51> Passing Criteria
  For Category 1 Products, the following are the applicable criteria:
  Bacteria: No less than 1.0 log reduction for the initial calculated count at 7 days, not less than 3.0 log reduction at 14 days, and no increase from the 14 days' count at 28 days.
  Yeast and Molds: No increase from the initial calculated count at 7, 14, and 28 days.
  For Category 2 Products, the following are the applicable criteria:

Bacteria: No less than 2.0 log reduction from the initial calculated count at 14 days, and no increase from the 14 days' count at 28 days.

Yeast and Molds: No increase from the initial calculated count at 14 and 28 days.

For Category 3 Products, the following are the applicable criteria:

Bacteria: No less than 1.0 log reduction from the initial count at 14 days, and no increase from the 14 days' count at 28 days.

Yeast and Molds: No increase from the initial calculated count at 14 and 28 days.

For Category 4 Products, the following are the applicable criteria:

Bacteria, Yeast, and Molds: No increase from the initial calculated count at 14 and 28 days.

Examples of orally acceptable preservatives include amino benzoic acid esters (i.e., "parabens") and their salts, carboxylic acids, like succinate, propionate, malate, ascorbate, sorbic acid and tartaric acid, bisulfites, borate, benzoates, benzalkonium chloride. Parabens are particularly preferred in the present invention as a preservative because they generally are effective in the range of pH 4-8. Examples of parabens suitable for oral formulations include methylparaben, ethylparaben, propylparaben, butylparaben. Methylparaben, ethylparaben, and combinations thereof are particularly preferred. On the other hand, other common oral formulation preservatives are generally only effective at more acidic pH and so would not work across the full range of contemplated pH values of the invention. For example, the effective upper pH limit for the following common preservatives is about: pH 6.5 for sorbates; pH 5.5 for propionates; and pH 4.5 for benzoates. The compositions of the invention do not contain benzoic acid.

The pharmaceutical composition of the present invention further contains an orally acceptable buffer. Suitable orally acceptable buffers specifically include acetate, carbonate, and phosphate, but for purposes of the present invention does not include citrate. The aforementioned buffers can be prepared using the free acids, various salt and hydrates of salts thereof, and combinations thereof. Potassium and sodium salts are particularly preferred in the compositions of the present invention. In other embodiments, mixtures of two or more orally acceptable buffers are used to obtain the appropriate buffering range. Mixtures of mono- and di-basic sodium or potassium phosphate salts can be used in certain embodiments to obtain a particular pH of the pharmaceutical composition. Phosphate buffers are particularly suitable for the invention and most preferred. Similarly, in other embodiments, carbonate and bicarbonate salts are used in suitable combination to obtain the desired pH of the pharmaceutical composition of the invention.

Exemplary orally acceptable buffers include the buffers listed in the following table, along with the pKa values.

| Buffer | Molecular Weight | PKa |
|---|---|---|
| BES | 213.2 | 7.15 |
| Bicine | 163.2 | 8.35 |
| BIS-Tris | 209.2 | 6.50 |
| BIS-Tris Propane | 282.4 | 6.80 |
| Boric acid | 61.8 | 9.24 |
| Cacodylic acid | 214.0 | 6.27 |
| CAPS | 221.3 | 10.40 |
| CHES | 207.3 | 9.50 |
| Citric Acid, Monohydrate | 210.1 | 4.76 |
| Glycine | 75.1 | 2.341 |
| Glycylglycine Free Base | 132.1 | 8.40 |
| HEPES Free Acid | 238.3 | 7.55 |
| HEPES Sodium Salt | 260.3 | 7.55 |
| Imidazole | 68.1 | 7.00 |
| MES, Free Acid | 195.2 | 6.15 |
| MES, Sodium Salt | 217.2 | 6.15 |
| MOPS, Free Acid | 209.3 | 7.20 |
| MOPS, Sodium Salt | 231.2 | 7.20 |
| PIPES, Free Acid | 302.4 | 6.80 |
| PIPES, Sodium Salt | 375.3 | 6.80 |
| PIPPS | 330.4 | 3.732 |
| Potassium Phosphate, Dibasic, Trihydrate, | 228.2 | 7.213 |
| Potassium Phosphate, Monobasic, | 136.1 | 7.213 |
| Sodium Phosphate, Dibasic | 142.0 | 7.213 |
| Sodium Phosphate, Monobasic | 120.0 | 7.213 |
| TAPS | 243.2 | 8.40 |
| TES | 229.3 | 7.50 |
| Tricine | 179.2 | 8.15 |
| Triethanolamine, HCl | 185.7 | 7.66 |
| Tris Base | 121.1 | 8.30 |
| Tris-HCl | 157.6 | 8.30 |
| Trisodium Citrate, Dihydrate, | 294.1 | — |

The pharmaceutical composition of the present invention contains in every embodiment a therapeutically effective amount of trimetazidine. The amount of trimetazidine can vary in various embodiments of the invention. In preferred embodiments, the amount of trimetazidine is present at less than 5% weight/volume (w/v), which can be measured either as the free base or as an acceptable salt. The maximum amount of trimetazidine is such that trimetazidine cannot effectively buffer the solution in the desired pH range. Preferred compositions contain, in certain embodiments, less than 2% w/v such as 0.2% to 2%, or less than 1% w/v, such as 0.1% to 1%, trimetazidine. Particularly preferred compositions contain less than 0.5% w/v trimetazidine, such as 0.1% to 0.5%, and or contain from 0.1% to 0.3% w/v trimetazidine, measured either as the free base or as an acceptable salt.

In certain embodiments, the pharmaceutical composition may also contain an antioxidant. An antioxidant is understood herein to mean certain embodiments which are substances that inhibits oxidation. Such antioxidants include, but are not limited to, ascorbyl palmitate, butylated hydroxyanisole, butylated hydroxytoluene, potassium metabisulfite, sodium metabisulfite, anoxomer and maleic acid BP.

In certain embodiments, the pharmaceutical composition may also contain a flavoring agent. A "flavoring agent" is understood herein to mean certain embodiments which are substances that alters the flavor of the composition during oral consumption. A type of "flavoring agent" would be a sweetener. Preferred sweeteners or flavoring agents would be microbially non-metabolizable. Especially preferred sweeteners or flavoring agents would be carbohydrates such as xylitol and sorbitol. Such flavoring agents include, but are not limited to, acacia syrup, anethole, anise oil, aromatic elixir, benzaldehyde, benzaldehyde elixir-compound, caraway, caraway oil, cardamom oil, cardamom seed, cardamom spirit, cardamom tincture-compound, cherry juice, cherry syrup, cinnamon, cinnamon oil, cinnamon water, citric acid, citric acid syrup, clove oil, coca, coca syrup, coriander oil, dextrose, eriodictyon, eriodictyon fluidextract, eriodictyon syrup aromatic, ethyl acetate, ethyl, vanillin, fennel oil, ginger, ginger fluidextract, ginger oleoresin, glucose, glycerin, *glycyrrhiza, glycyrrhiza* elixir, *glycyrrhiza* extract, glycyrrhiza extract-pure, glycyrrhiza fluidextract, glycyrrhiza syrup, honey, non-alcoholic elixir, lavender oil, citrus extract or oil, lemon oil, lemon tincture, mannitol, methyl salicylate, nutmeg oil, orange-bitter-elixir, orange-bitter-oil, orange flower oil, orange flower water, orange oil, orange peel-bitter, orange-peel-sweet-tincture, orange spirit-compound, compound, orange syrup, peppermint, peppermint oil, peppermint spirit, peppermint water, phenylethyl alcohol, raspberry juice, raspberry syrup, rosemary oil, rose oil, rose water, saccharin, saccharin calcium, saccharin sodium, sarsaparilla syrup, sorbitol solution, spearmint, spearmint oil, sucrose, syrup, thyme oil, tolu balsam, tolu balsam syrup, vanilla, vanilla tincture, vanillin or wild cherry syrup.

Other embodiments of the present invention comprise a method of treatment using the pharmaceutical compositions described herein. Such methods of treatment comprise administering a stable oral liquid pharmaceutical dosage form of trimetazidine having a pH of about pH 4 to about pH 8, comprising a therapeutically effective amount of trimetazidine or a pharmaceutically acceptable salt thereof, one or more orally acceptable buffers, and one or more orally acceptable preservatives that is effective in said pH range. In other embodiments of the method, the various embodiments of the pharmaceutical formulations described herein can be used to affect the desired treatment.

In preferred embodiments, the oral liquid pharmaceutical dosage form of trimetazidine is administered to a patient who is suffering from renal insufficiency or who is at risk of suffering from renal insufficiency. Renal insufficiency is generally defined with reference to serum creatinine concentrations that may be used to estimate glomerular filtration rate calculate creatinine clearance rate. Generally, renal insufficiency is defined as a serum creatinine level exceeding 1.5 mg/dL or a creatinine clearance rate of less than 60 mL/min. Renal failure is commonly defined as a serum creatinine level of 2 mg/dL or more or a creatinine clearance rate of less than 30 mL/min. In a preferred embodiment, treated subjects are at risk for or have renal insufficiency or renal failure as a consequence of liver cirrhosis. In other embodiments, treated subjects will have renal insufficiency or renal failure due to other reasons, such as age-related decline, acute kidney injury, chronic kidney injury, polycystic kidney disease, drug-induced nephropathy (including chemotherapy-induced nephropathy, idiopathic nephropathy and nephropathy due to other known causes. Such with renal insufficiency or renal impairment may be treated for their kidney problems or may be treated for other maladies treatable with trimetazidine, such as angina.

A typical method will reduce dosing by ⅓ for renally impaired subjects and then by ⅔ for subjects with renal failure. Thus, if a patient is receiving 60 mg of trimetazidine per day without renal insufficiency, a patient with renal insufficiency may receive 40 mg per day and a patient with renal failure may receive 20 mg per day. In one dosing regimen, patients without renal impairment receive 10 mL of a 2 mg/ml trimetazidine solution three times per day for a total of 60 mg/day. With renal impairment, patients will receive 6.7 mL of a 2 mg/ml trimetazidine solution three times per day for a total of 40 mg/day. With renal failure, patients will receive 3.3 mL of a 2 mg/mL trimetazidine solution three times per day for a total of 20 mg/day.

Embodiments of the present disclosure can be further defined by reference to the following examples, which are meant to exemplify aspects of the invention and should in no way be construed as limiting. It will be apparent to those skilled in the art that many modifications, both to materials and methods, can be practiced without departing from the scope of the present disclosure. As used herein and in the appended claims, the singular forms "a," "or," and "the" include plural referents unless the context clearly dictates otherwise.

EXAMPLES

Example 1: Excipient Compatibility

To identify preferred excipients that are incompatible with trimetazidine, samples were prepared as binary formulations composed of trimetazidine and a single excipient or buffer. All of the samples were diluted in sterile water, or aqueous buffer, at pH 6.0±0.1. All samples were packaged in 20 mL scintillation vials protected from light with PTFE caps.

| Item No. | Ingredient | IIG Limit | Proposed Usage Level | Function |
|---|---|---|---|---|
| 1 | Trimetazidine | NA | 2 mg/mL | Active ingredient |
| 2 | Citric Acid Monohydrate, USP | 20 mg/mL | 1.91 mg/mL | Buffer |
| 3 | Trisodium Citrate Dihydrate | 18 mg/mL | 2.68 mg/mL | Buffer |
| 4 | Sodium Phosphate Dibasic Dihydrate, USP | 8 mg/mL | 0.54 mg/mL | Buffer |
| 5 | Sodium Phosphate Monobasic Monohydrate, USP | 12.9 mg/mL | 11.0 mg/mL | Buffer |
|   | Methylparaben Sodium | 2.6 mg/mL | 1.5 mg/mL | Preservative |
| 6 | Propylparaben Sodium | 0.23 mg/mL | 0.23 mg/mL | Preservative |
| 7 | Sucralose | 40 mg/mL | 0.2-0.4 mg/mL | Sweetener |
| 8 | Maltitol Solution, USP | 750 mg/mL | 10 mg/mL | Sweetener |
| 9 | Xanthan Gum NF-C | 3 mg/mL | 0.5 mg/mL | Viscosity Modifier |
| 10 | Orange Flavor, Artificial | NA | 1 mg/mL | Flavor/Taste Masking |
| 11 | Peppermint | NA | 1 mg/mL | Flavor/Taste masking |
| 12 | Saline | NA | 0.9% | Diluent |
| 13 | Water | NA | QS | Diluent |

| | Sample Composition | | | | | |
|---|---|---|---|---|---|---|
| Ingredient | 1 | 2 | 3 | 4 | 5 | 6 |
| Trimetazidine | 40 mg | 40 mg | 40 mg | 40 mg | 40 mg | 40 mg |
| Citrate Buffer (100 mM) | 20 mL | | | | | |

-continued

| Ingredient | | | | | |
|---|---|---|---|---|---|
| Phosphate Buffer (100 mM) | 20 mL | | | | |
| Citrate/Phosphate Buffer (120 mM) | | 20 mL | | | |
| Methylparaben Sodium | | | 40 mg | | |
| Propylparaben Sodium | | | | 40 mg | |
| Sucralose | | | | | 40 mg |
| Maltitol Solution, USP | | | | | |
| Xanthan Gum NF-C | | | | | |
| Orange Flavor, Artificial | | | | | |
| Peppermint | | | | | |
| 0.9% Saline (pH 6.0) | | | | | |
| Water pH 6.0 | | | 20 mL | 20 mL | 20 mL |

| | Sample Composition | | | | |
|---|---|---|---|---|---|
| Ingredient | 7 | 8 | 9 | 10 | 11 |
| Trimetazidine | 40 mg | 40 mg | 40 mg | 40 mg | 40 mg |
| Citrate Buffer (100 mM) | | | | | |
| Phosphate Buffer (100 mM) | | | | | |
| Citrate/Phosphate Buffer (120 mM) | | | | | |
| Methylparaben Sodium | | | | | |
| Propylparaben Sodium | | | | | |
| Sucralose | | | | | |
| Maltitol Solution, USP | 40 mg | | | | |
| Xanthan Gum NF-C | | 40 mg | | | |
| Orange Flavor, Artificial | | | 40 mg | | |
| Peppermint | | | | 40 mg | |
| 0.9% Saline (pH 6.0) | | | | | 20 mL |
| Water pH 6.0 | 20 mL | 20 mL | 20 mL | 20 mL | |

Samples were stored upright under the following conditions for 8 weeks at 40° C./75% relative humidity. Samples were tested according the following table:

| Test | Test Method | Method Type | Specification |
|---|---|---|---|
| pH | USP<791> | Potentiometric | |
| Appearance | Visual | Visual | Report color, clarity, presence/absence of particulate matter. |
| % Assay | TBD[1] | HPLC/UV | NMT 5% abs diff of T = 0 |
| Related Compounds | TBD[1] | HPLC/UV | Report Results >0.05% % Area Relative to the API |

Appearance Results

| | | TMZ | | |
|---|---|---|---|---|
| Sample | Run# | T = 0 | T = 30 days[1] | T = 60 days |
| API + Water (pH 6.0) | (Control) | Clear, transparent, free of particulate matter | Clear, transparent, some particulate present | Clear, transparent, some particulate present |
| API + Citrate Buffer (100 mM) | 1 | Clear, transparent, free of particulate matter | Clear, transparent, some particulate present | Clear, transparent, some particulate present |
| API + Phosphate Buffer (100 mM) | 2 | Clear, transparent, free of particulate matter | Clear, transparent, some particulate present | Clear, transparent, some particulate present |
| API + Citrate/Phosphate Buffer (120 mM) | 3 | Clear, transparent, free of particulate matter | Clear, transparent, some particulate present | Clear, transparent, some particulate present |
| API + Water (pH 6.0) + Methylparaben Sodium | 4 | Clear, transparent, free of particulate matter | Clear, transparent, some particulate present | Clear, transparent, some particulate present |
| API + Water (pH 6.0) + Propylparaben Sodium | 5 | Clear, transparent, significant particulate matter present | Clear, transparent, some particulate present | Clear, transparent, some particulate present |
| API + Water (pH 6.0) + Sucralose | 6 | Clear, transparent, free of particulate matter | Clear, transparent, some particulate present | Clear, transparent, some particulate present |
| API + Water (pH 6.0) + Maltitol Solution, USP | 7 | Clear, transparent, free of particulate matter | Clear, transparent, some particulate present | Clear, transparent, some particulate present |
| API + Water (pH 6.0) + Xanthan Gum | 8 | Clear, transparent, free of particulate matter | Clear, transparent, some particulate present | Clear, transparent, some particulate present |
| API + Water (pH 6.0) + Orange Flavor | 9 | Clear, transparent, free of particulate matter | Clear, transparent, some particulate present | Clear, transparent, some particulate present |
| API + Water (pH 6.0) + Peppermint Flavor | 10 | Clear, transparent, free of particulate matter | Clear, transparent, some particulate present | Clear, transparent, some particulate present |

TMZ

| Sample | Run# | T = 0 | T = 30 days[1] | T = 60 days |
|---|---|---|---|---|
| API + 0.9% Saline (pH 6.0) | 11 | Clear, transparent, free of particulate matter | Clear, transparent, some particulate present | Clear, transparent, some particulate present |
| API + Water (pH 6.0) + Ethylparaben | 12 | Clear, transparent, significant particulate present[2] | Clear, transparent, some particulate present | Clear, transparent, some particulate present |

[1] Particulates are non-microbial amorphous fibers which appear in all of the API sample and placebos. Comparison of filtered and non-filtered samples do not indicate and type of precipitation. The likely source of the particulate matter is from the packaging components used for the study.
[2] Appears to be undissolved ethylparaben

Placebo

| Sample | Run# | T = 0 | T = 30 days | T = 60 days |
|---|---|---|---|---|
| Control - Water (pH 6.0) | (Control) | Clear, transparent, free of particulate matter | Clear, transparent, some particulate present | Clear, transparent, free of particulate matter |
| Citrate Buffer (100 mM) | 1 | Clear, transparent, free of particulate matter | Clear, transparent, some particulate present | Clear, transparent, some particulate present |
| Phosphate Buffer (100 mM) | 2 | Clear, transparent, free of particulate matter | Clear, transparent, some particulate present | Clear, transparent, some particulate present |
| Citrate/Phosphate Buffer (120 mM) | 3 | Clear, transparent, free of particulate matter | Clear, transparent, some particulate present | Clear, transparent, some particulate present |
| Methylparaben Sodium + Water (pH 6.0) | 4 | Clear, transparent, free of particulate matter | Clear, transparent, some particulate present | Clear, transparent, some particulate present |
| Propylparaben Sodium + Water (pH 6.0) | 5 | Clear, transparent, free of particulate matter | Clear, transparent, some particulate present | Clear, transparent, some particulate present |
| Sucralose + Water (pH 6.0) | 6 | Clear, transparent, free of particulate matter | Clear, transparent, some particulate present | Clear, transparent, some particulate present |
| Maltitol Solution + Water (pH 6.0) | 7 | Clear, transparent, free of particulate matter | Clear, transparent, some particulate present | Clear, transparent, some particulate present |
| Xanthan Gum NF-C + Water (pH 6.0) | 8 | Clear, transparent, free of particulate matter | Clear, transparent, some particulate present | Clear, transparent, some particulate present |
| Orange Flavor + Water (pH 6.0) | 9 | Clear, transparent, free of particulate matter | Clear, transparent, some particulate present | Clear, transparent, some particulate present |
| Peppermint Flavor + Water (pH 6.0) | 10 | Clear, transparent, free of particulate matter | Clear, transparent, some particulate present | Clear, transparent, some particulate present |
| 0.9% Saline (pH 6.0) | 11 | Clear, transparent, free of particulate matter | Clear, transparent, some particulate present | Clear, transparent, some particulate present |
| Ethylparaben + Water (pH 6.0) | 12 | Clear, transparent, significant particulate present[1] | Clear, transparent, some particulate present | Clear, transparent, some particulate present |

[1] Appears to be undissolved ethylparaben

Trimetazidine Assay Results

Placebo samples were not analyzed.

Trimetazidine

| Sample | Run# | T = 0 | T = 30 days | T = 60 days |
|---|---|---|---|---|
| API + Water (pH 6.0) | (Control) | 102.91% | 93.29% | 94.55% |
| API + Citrate Buffer (100 mM) | 1 | 105.54% | 98.33% | 98.88% |
| API + Phosphate Buffer (100 mM) | 2 | 97.23% | 97.51% | 96.65% |
| API + Citrate/Phosphate Buffer (120 mM) | 3 | 97.40% | 97.29% | 98.38% |
| API + Water (pH 6.0) + Methylparaben Sodium | 4 | 95.67% | 98.74% | 99.56% |
| API + Water (pH 6.0) + Propylparaben Sodium | 5 | 88.31% | 92.60% | 94.24% |
| API + Water (pH 6.0) + Sucralose | 6 | 95.83% | 99.04% | 98.54% |
| API + Water (pH 6.0) + Maltitol Solution, USP | 7 | 90.21% | 92.99% | 92.52% |
| API + Water (pH 6.0) + Xanthan Gum | 8 | 99.25% | 99.22% | 97.16% |
| API + Water (pH 6.0) + Orange Flavor | 9 | 104.86% | 97.55% | 97.64% |
| API + Water (pH 6.0) + Peppermint Flavor | 10 | 98.40% | 99.15% | 99.28% |
| API + 0.9% Saline (pH 6.0) | 11 | 97.64% | 100.02% | 90.92% |
| API + Water (pH 6.0) + Ethylparaben | 12 | 97.25% | 99.17% | 99.07% |

Related Compounds

Full results are reported for trimetazidine samples. Only paraben results are presented for placebo samples.

Trimetazidine

| Sample | Run# | T = 0 | T = 30 days[1] | T = 60 days |
|---|---|---|---|---|
| API + Water (pH 6.0) | (Control) | ND | ND | ND |
| API + Citrate Buffer (100 mM) | 1 | ND | RRT 0.09-0.07% RRT 1.90-0.06% Total - 0.13% | RRT 0.09-0.06% RRT 0.134-1.12% RRT 0.22-0.05% Total- 1.23% |

Trimetazidine

| Sample | Run# | T = 0 | T = 30 days[1] | T = 60 days |
|---|---|---|---|---|
| API + Phosphate Buffer (100 mM) | 2 | ND | ND | RRT 0.25-0.18% RRT 1.31-0.17% Total-0.35% |
| API + Citrate/Phosphate Buffer (120 mM) | 3 | ND | RRT 0.16-0.24% Total-0.24% | RRT 0.16-0.30% Total-0.30% |
| API + Water (pH 6.0) + Methylparaben Sodium | 4 | pHBA-0.79% | pHBA-3.26% | pHBA-6.09% |
| API + Water (pH 6.0) + Propylparaben Sodium | 5 | pHBA-1.17% | pHBA-1.53% | pHBA-1.69% |
| API + Water (pH 6.0) + Sucralose | 6 | ND | ND | ND |
| API + Water (pH 6.0) + Maltitol Solution, USP | 7 | ND | ND | ND |
| API + Water (pH 6.0) + Xanthan Gum | 8 | ND | ND | RRT 1.31-0.08% Total-0.08% |
| API + Water (pH 6.0) + Orange Flavor | 9 | ND | RRT 1.90-0.08% Total-0.08% | ND |
| API + Water (pH 6.0) + Peppermint Flavor | 10 | ND | ND | ND |
| API + 0.9% Saline (pH 6.0) | 11 | ND | ND | ND |
| API + Water (pH 6.0) + Ethylparaben | 12 | ND | pHBA-0.33%* | RRT 0.107-0.19% RRT 0.265-0.07% Total: 0.26% (pHBA-0.71%) |

[1]Relative Retention Time 1.90 identified as process impurity B

Placebo Related Compounds Results - Stability Condition: Darwin 40° C./75% RH

| Sample | Run# | T = 0 | T = 30 days | T = 60 days |
|---|---|---|---|---|
| Methylparaben Sodium + Water (pH 6.0) | 4 | pHBA-3.62% | pHBA-156.15% | pHBA-227.86% |
| Propylparaben Sodium + Water (pH 6.0) | 5 | pHBA-9.55% | pHBA-76.31% | pHBA-119.80% |
| Ethylparaben + Water (pH 6.0) | 12 | ND | pHBA-0.74% | pHBA: 1.40% | pH Results

Trimetazidine

| Sample | Run# | T = 0 | T = 30 days | T = 60 days |
|---|---|---|---|---|
| API + Water (pH 6.0) | (Control) | 5.91 | 6.27 | 6.32 |
| API + Citrate Buffer (100 mM) | 1 | 6.02 | 5.97 | 6.02 |
| API + Phosphate Buffer (100 mM) | 2 | 5.94 | 5.87 | 5.89 |
| API + Citrate/Phosphate Buffer (120 mM) | 3 | 5.90 | 5.83 | 5.86 |
| API + Water (pH 6.0) + Methylparaben Sodium | 4 | 6.06 | 6.18 | 6.11 |
| API + Water (pH 6.0) + Propylparaben Sodium | 5 | 5.88 | 5.97 | 5.90 |
| API + Water (pH 6.0) + Sucralose | 6 | 6.18 | 6.39 | 6.37 |
| API + Water (pH 6.0) + Maltitol Solution, USP | 7 | 5.96 | 6.36 | 6.35 |
| API + Water (pH 6.0) + Xanthan Gum | 8 | 5.85 | 6.20 | 6.21 |
| API + Water (pH 6.0) + Orange Flavor | 9 | 5.88 | 6.48 | 6.29 |
| API + Water (pH 6.0) + Peppermint Flavor | 10 | 6.04 | 6.31 | 6.13 |
| API + 0.9% Saline (pH 6.0) | 11 | 6.10 | 6.85 | 6.69 |
| API + Water (pH 6.0) + Ethylparaben | 12 | 3.32 | 3.32 | 3.10 |

Placebo

| Sample | Run# | T = 0 | T = 30 days | T = 60 days |
|---|---|---|---|---|
| Control - Water (pH 6.0) | (Control) | 6.90 | 7.68 | 7.09 |
| Citrate Buffer (100 mM) | 1 | 6.28 | 6.18 | 6.22 |
| Phosphate Buffer (100 mM) | 2 | 6.08 | 6.07 | 6.09 |
| Citrate/Phosphate Buffer (120 mM) | 3 | 6.06 | 6.06 | 6.08 |
| Methylparaben Sodium + Water (pH 6.0) | 4 | 9.73 | 8.87 | 8.54 |
| Propylparaben Sodium + Water (pH 6.0) | 5 | 9.70 | 9.17 | 8.96 |
| Sucralose + Water (pH 6.0) | 6 | 7.41 | 7.29 | 6.93 |
| Maltitol Solution + Water (pH 6.0) | 7 | 7.50 | 6.95 | 6.96 |
| Xanthan Gum NF-C + Water (pH 6.0) | 8 | 7.01 | 7.30 | 6.90 |
| Orange Flavor + Water (pH 6.0) | 9 | 8.04 | 7.30 | 7.59 |
| Peppermint Flavor + Water (pH 6.0) | 10 | 6.69 | 6.02 | 5.79 |
| 0.9% Saline (pH 6.0) | 11 | 6.59 | 7.01 | 8.18 |
| Ethylparaben + Water (pH 6.0) | 12 | 6.79 | 6.65 | 6.29 |

Example 2: Microbial Testing

Three prototypes, the compositions of which are set out below, were tested for preservative activity as follows.

Batch 139-18001 (85% AET with Xanthan Gum)

| No. | Ingredient | % w/v | mg/mL | Amount (g) |
|---|---|---|---|---|
| 1 | Trimetazidine | 0.25 | 2.50 | 0.63 |
| 2 | Sodium Phosphate Monobasic Monohydrate | 0.75 | 7.50 | 1.88 |
| 3 | Sodium Phosphate Dibasic Dihydrate | 0.32 | 3.15 | 0.79 |
| 4 | Methylparaben Sodium | 0.17 | 1.70 | 0.43 |
| 5 | Ethylparaben Sodium | 0.03 | 0.34 | 0.09 |
| 6 | Sucralose | 0.25 | 2.50 | 0.63 |
| 7 | Xanthan Gum | 0.10 | 1.00 | 0.25 |
| 8 | Peppermint flavor (artificial) | 0.05 | 0.50 | 0.13 |
| 9 | Water | 98.08 | 980.81 | 245.20 |
| | Total | 100.00 | 1000.00 | 250.00 |

Results

At day 14 after inoculation *E. coli* demonstrated more than a 5.0 log reduction, *S. aureus* demonstrated more than a 4.8 log reduction, *B. cepacia* demonstrated more than a 4.3 log reduction; *P. aeruginosa* demonstrated a 1.7 log reduction. *C. albicans* and *A. brasiliensis* demonstrated no growth at day 14.

At day 28 after inoculation E. coli demonstrated more than a 5.0 log reduction, S. aureus demonstrated more than a 4.8 log reduction, B. cepacia demonstrated more than a 4.3 log reduction; P. aeruginosa demonstrated a 4.0 log reduction. C. albicans and A. brasiliensis demonstrated no growth at day 28.

Interpretation

A test sample meets the USP Specifications for Category 3 products if there is a 1.0 log reduction of bacterial organisms at day 14 with no increase at day 28. Fungal organisms must demonstrate no increase from the initial inoculum during the 28-day test period.

Conclusion

This sample passes the USP Antimicrobial Preservative Effectiveness Test for Category 3 products.

| Batch 139-18002 (85% AET without Xanthan Gum) | | | | |
|---|---|---|---|---|
| No. | Ingredient | % w/v | mg/mL | Amount (g) |
| 1 | Trimetazidine | 0.25 | 2.55 | 0.64 |
| 2 | Sodium Phosphate Monobasic Monohydrate | 0.75 | 7.50 | 1.88 |
| 3 | Sodium Phosphate Dibasic Dihydrate | 0.32 | 3.15 | 0.79 |
| 4 | Methylparaben Sodium | 0.17 | 1.70 | 0.43 |
| 5 | Ethylparaben Sodium | 0.03 | 0.34 | 0.09 |
| 6 | Sucralose | 0.25 | 2.50 | 0.63 |
| 7 | Peppermint flavor (artificial) | 0.05 | 0.50 | 0.13 |
| 8 | Water | 98.18 | 981.76 | 245.44 |
| | Total | 100.00 | 1000.00 | 250.00 |

Results

At day 14 after inoculation E. coli demonstrated more than a 5.0 log reduction, S. aureus demonstrated more than a 4.8 log reduction, B. cepacia demonstrated more than a 4.3 log reduction; P. aeruginosa demonstrated a 1.5 log reduction. C. albicans and A. brasiliensis demonstrated no increase at day 14.

At day 28 after inoculation E. coli demonstrated more than a 5.0 log reduction, S. aureus demonstrated more than a 4.8 log reduction, B. cepacia demonstrated more than a 4.3 log reduction; P. aeruginosa demonstrated more than a 4.5 log reduction. C. albicans and A. brasiliensis demonstrated no increase at day 28.

Interpretation

A test sample meets the USP Specifications for Category 3 products if there is a 1.0 log reduction of bacterial organisms at day 14 with no increase at day 28. Fungal organisms must demonstrate no increase from the initial inoculum during the 28-day test period.

Conclusion

This sample passes the USP Antimicrobial Preservative Effectiveness Test for Category 3 products

| Batch 139-18003 (75% AET without Xanthan Gum) | | | | |
|---|---|---|---|---|
| No. | Ingredient | % w/v | mg/mL | Amount (g) |
| 1 | Trimetazidine | 0.25 | 2.50 | 0.63 |
| 2 | Sodium Phosphate Monobasic Monohydrate | 0.75 | 7.50 | 1.88 |
| 3 | Sodium Phosphate Dibasic Dihydrate | 0.32 | 3.15 | 0.79 |
| 4 | Methylparaben Sodium | 0.15 | 1.50 | 0.38 |
| 5 | Ethylparaben Sodium | 0.03 | 0.30 | 0.08 |
| 6 | Sucralose | 0.25 | 2.50 | 0.63 |
| 7 | Peppermint flavor (artificial) | 0.05 | 0.50 | 0.13 |
| 8 | Water | 98.21 | 982.05 | 245.51 |
| | Total | 100.00 | 1000.00 | 250.00 |

Results

At day 14 after inoculation E. coli demonstrated a 3.7 log reduction, S. aureus demonstrated a 4.5 log reduction, B. cepacian demonstrated a 4.0 log reduction; P. aeruginosa demonstrated a 4.5 log reduction. C. albicans and A. brasiliensis demonstrated no increase at day 14.

At day 28 after inoculation E. coli demonstrated a 3.3 log reduction, S. aureus demonstrated more than a 4.8 log reduction, B. cepacia demonstrated more than a 4.3 log reduction; P. aeruginosa demonstrated more than a 4.5 log reduction. C. albicans and A. brasiliensis demonstrated no increase at day 28.

Interpretation

A test sample meets the USP Specifications for category 3 products if there is a 1.0 log reduction of bacterial organisms at day 14
with no increase at day 28. Fungal organisms must demonstrate no increase from the initial inoculum during the 28 day test period.

Conclusion

This sample passes the USP Antimicrobial Preservative Effectiveness Test for Category 3 products.

What is claimed is:

1. A stable oral liquid pharmaceutical composition of trimetazidine having a pH of pH 5 to pH 7, comprising a therapeutically effective amount of trimetazidine or a pharmaceutically acceptable salt thereof, one or more orally acceptable buffers, and one or more orally acceptable preservatives that is effective in said pH range.

2. The pharmaceutical composition according to claim 1, wherein the one or more orally suitable buffers comprises a phosphate buffer.

3. The pharmaceutical composition according to claim 1 which comprises a single orally suitable buffer selected from the group consisting of acetate, carbonate, and phosphate.

4. The pharmaceutical composition according to claim 3, wherein the pH of the composition is from about 5.5 to about 6.5.

5. The pharmaceutical composition according to claim 4, wherein the one or more orally acceptable preservatives includes methylparaben.

6. The pharmaceutical composition according to claim 5, wherein the one or more orally acceptable preservatives includes ethylparaben.

7. The pharmaceutical composition according to claim 1, wherein the therapeutically effective amount of trimetazidine or a pharmaceutically acceptable salt thereof is less than 5% w/v trimetazidine as free base or a pharmaceutically acceptable salt.

8. The pharmaceutical composition according to claim 7, wherein the therapeutically effective amount of trimetazidine or a pharmaceutically acceptable salt thereof is from about 0.1% to about 2% w/v trimetazidine as free base or a pharmaceutically acceptable salt.

9. The pharmaceutical composition according to claim 8, wherein the therapeutically effective amount of trimetazidine or a pharmaceutically acceptable salt thereof is from about 0.1% to about 1% w/v trimetazidine as free base or a pharmaceutically acceptable salt.

10. The pharmaceutical composition according to claim 9, wherein the therapeutically effective amount of trimetazidine or a pharmaceutically acceptable salt thereof is from about 0.1% to about 0.5% trimetazidine as free base or a pharmaceutically acceptable salt; the one or more orally acceptable buffers is a phosphate buffer; and the one or more orally acceptable preservatives is one or more parabens.

11. The pharmaceutical composition according to claim 9, wherein the wherein the therapeutically effective amount of trimetazidine or a pharmaceutically acceptable salt thereof is from about 0.1% to about 0.3% trimetazidine as free base or a pharmaceutically acceptable salt; the one or more orally acceptable buffers is a phosphate buffer; and the one or more orally acceptable preservatives is one or more parabens.

12. A method of treating a condition treatable with trimetazidine in a patient having a said condition and who has a decreased tolerance for acidic or highly basic oral solutions, comprising administering to said patient the composition according to claim 1.

13. A method of treating a condition treatable with trimetazidine in a patient having a said condition and who has a decreased tolerance for acidic or highly basic oral solutions, comprising administering to said patient the composition according to claim 11.

14. The method according to claim 12, wherein the patient has liver cirrhosis.

15. The method according to claim 14, wherein said patient has renal insufficiency.

16. The method according to claim 12, wherein the therapeutically effective amount of trimetazidine or a pharmaceutically acceptable salt thereof is from about 0.1% to about 1% w/v trimetazidine as free base or a pharmaceutically acceptable salt; and wherein the one or more orally acceptable buffers is a single buffer selected from the group consisting of acetate, carbonate, and phosphate, and wherein the pH is from about 5.5 to about 6.5.

17. The method according to claim 16, wherein the preservative is a mixture of methylparaben sodium and ethylparaben sodium.

* * * * *